(12) United States Patent
Hatano et al.

(10) Patent No.: US 8,422,014 B2
(45) Date of Patent: Apr. 16, 2013

(54) METHOD FOR INSPECTING DEFECT OF ARTICLE TO BE INSPECTED

(75) Inventors: Tatsuhiko Hatano, Kasugai (JP); Kouichi Miyashita, Kasugai (JP); Isao Shikata, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 421 days.

(21) Appl. No.: 12/712,419

(22) Filed: Feb. 25, 2010

(65) Prior Publication Data

US 2010/0201983 A1    Aug. 12, 2010

Related U.S. Application Data

(63) Continuation of application No. PCT/JP2008/065691, filed on Sep. 1, 2008.

(30) Foreign Application Priority Data

Aug. 30, 2007   (JP) ................................. 2007-224083

(51) Int. Cl.
   *G01N 21/00*   (2006.01)
(52) U.S. Cl.
   USPC ....................................... 356/337; 356/237.1
(58) Field of Classification Search ......................... None
   See application file for complete search history.

(56) References Cited

U.S. PATENT DOCUMENTS

| 5,463,462 | A * | 10/1995 | Ohnishi et al. ................. 356/521 |
| 2003/0112437 | A1* | 6/2003 | Enomoto et al. ............... 356/402 |
| 2008/0144024 | A1* | 6/2008 | Nakano et al. ............. 356/237.4 |
| 2009/0122303 | A1* | 5/2009 | Nakano et al. ............. 356/237.2 |
| 2010/0106443 | A1* | 4/2010 | Shimura et al. ................. 702/81 |
| 2010/0265496 | A1* | 10/2010 | Nakano et al. ............. 356/237.5 |
| 2011/0063603 | A1* | 3/2011 | Nakano et al. ................. 356/51 |

FOREIGN PATENT DOCUMENTS

| CN | 1460177 A | 12/2003 |
| JP | 64-003545 A1 | 1/1989 |
| JP | 01-320445 A1 | 12/1989 |
| JP | 11-326223 A1 | 11/1999 |
| JP | 2000-162141 A1 | 6/2000 |
| JP | 2000-216208 A1 | 8/2000 |
| JP | 2002-357562 A1 | 12/2002 |

OTHER PUBLICATIONS

Chinese Office Action dated Mar. 21, 2012 (with English translation).

* cited by examiner

*Primary Examiner* — Mussa A Shaawat
(74) *Attorney, Agent, or Firm* — Burr & Brown

(57) ABSTRACT

A method of inspecting defects in an inspection target includes (1) a step of supplying a particle-containing gas to one end face of the inspection target under pressure, applying in parallel a first laser beam to the vicinity of the other end face of the inspection target, and photographing such end face from a position vertical to such end face, (2) a step of supplying a particle-containing gas to the one end face of the inspection target under pressure, applying in parallel a second laser beam to the vicinity of the other end face of the inspection target, and photographing such end face from a position vertical to such end face, and (3) a step of specifying defects in the inspection target from photographic results obtained by the steps (1) and (2).

12 Claims, 6 Drawing Sheets

METHOD FOR INSPECTING DEFECT OF ARTICLE TO BE INSPECTED

FIELD OF THE INVENTION

The present invention relates to a method and an apparatus that detects a defect in an inspection target. More particularly, the present invention relates to a method and an apparatus that can detect a defect in an inspection target with high sensitivity and allow detection and a post-treatment to be completed within a short time.

BACKGROUND OF THE INVENTION

Examples of an inspection target that must be inspected for detecting a defect include a porous article and the like. A porous article has been widely used for filters, catalyst carriers, and the like. For example, a porous article has been used for an exhaust gas purification apparatus for a heat engine (e.g., internal combustion engine) or combustion equipment (e.g., boiler), a liquid/gaseous fuel reforming apparatus, a service water/sewage purification apparatus, and the like. A porous article having a honeycomb shape has been used as a diesel particulate filter or a high-temperature gas collection apparatus that traps and removes particulate matter contained in a dust-containing fluid (e.g., exhaust gas discharged from a diesel engine).

A porous article used for such purposes traps and removes unnecessary particulate matter when the treatment target fluid passes through the pores formed in the porous article, or allows the treatment target fluid to come in contact with a catalyst supported on the surface of the porous article and inside the pores formed in the porous article, for example. In order to improve the removal/contact efficiency, a porous article in the shape of a thin film or wall is normally formed into a tubular shape, a monolith shape, a honeycomb shape, or the like to increase the contact area with the treatment target fluid. The porous article cannot achieve the desired filtration performance and catalyst carrier performance if a large hole (defect) is formed through the wall (film) of the porous article. A non-porous article may not achieve the desired performance when a hole (defect) is formed in the non-porous article. A defect in a porous article or a non-porous article can be simply inspected by naked eye observation.

However, it may be difficult to inspect a defect in a porous article or a non-porous article depending on the shape of the inspection target (i.e., porous article or non-porous article) and the position and the size of the defect. For example, a honeycomb structure has a number of through holes that are partitioned by a partition wall and formed through the honeycomb structure in the axial direction. The ends of the through holes may be alternately plugged so that particulate matter is trapped and removed by the porous partition wall. A defect in the partition wall of such a honeycomb structure cannot be observed from the outside.

A defect inspection method that includes generating (producing) particles, introducing the generated particles into the inspection target, and applying light with high directivity to the particles discharged from the inspection target so that the light travels near the inspection target to visualize the particles, has been known (Patent Document 1).

FIG. 6 is a schematic front view showing an apparatus used for this method. Particles and air are respectively supplied from a particle source 15 and an air source 17 to form particle-containing air 19. The particle-containing air 19 is supplied from a particle supply means 1 to one end face of an inspection target 11 under a given pressure. The particle-containing air 19 then passes through the inspection target 11, and is discharged through the other end face of the inspection target 11 as particle-containing air 21. A laser beam irradiation means 3 is disposed so that a laser beam 23 travels near the other end face of the inspection target 11. The particle-containing air 21 that has passed through the inspection target is exposed to the laser beam 23.

The particles contained in the particle-containing air 19 and having a particle size equal to or larger than a given particle size cannot pass through the inspection target 11, and are trapped by the inspection target 11. However, when the inspection target 11 has a defect (e.g., cracks or holes), the particles having a particle size equal to or larger than the given particle size pass through the defect. Since the laser beam 23 is scattered to a large extent by the particles having a particle size equal to or larger than the given particle size, a bright spot is formed corresponding to the defect. The defect can be detected by detecting the bright spot using a light detection means 7.

A defect in an inspection target having a shape that does not allow external defect inspection can be detected with high sensitivity by utilizing the above method and apparatus.
Patent Document 1: JP-A-2002-357562

SUMMARY OF THE INVENTION

According to the above method, however, light with high directivity (laser beam) is scattered by the particles, reflected by the edge of the end face of the inspection target (i.e., the edge shines), and serves as noise. FIG. 7 is a view showing such a state. FIG. 7 is an enlarged cross-sectional view showing a through hole 27 of a honeycomb structure (inspection target) and a partition wall 25 that defines the through hole 27. The laser beam 23 is scattered upon collision with the particles. The laser beam scattered in the direction of the light detection means 7 is detected by the light detection means 7 as a bright spot 33. This makes it possible to detect the presence of a particle 29 (i.e., defect). In this case, the edge of the partition wall 25 that is opposite to the laser beam irradiation means across the through hole 27 shines due to the laser beam scattered by the particle 29, and is detected by the light detection means 7 as a bright spot 33. FIG. 8 is a schematic plan view of FIG. 7. When the laser beam is applied to the end face in the diagonal direction of the square through hole 27, the edge of the partition wall 25 that is opposite to the laser beam irradiation means shines in the shape of the letter "L" to form a bright spot 33. The bright spot 33 cannot be distinguished from the bright spot that occurs due to the defect.

In view of the above situation, an object of the present invention is to provide a defect inspection method and a defect inspection apparatus that reduce the effects of noise and can detect a defect with high sensitivity.

The inventors of the present invention conducted extensive studies in order to achieve the above object. As a result, the inventors found that the above object can be achieved by the following method and apparatus. This finding has led to the completion of the present invention.

Specifically, the present invention provides the following method and apparatus.

[1] A method of inspecting a defect in an inspection target, the method comprising: (1) a step of supplying a particle-containing gas to one end face of the inspection target under pressure, applying a first laser beam so that the first laser beam travels near the other end face of the inspection target parallel to the other end face of the inspection target, and photographing the other end face of the inspection target perpendicularly to the other end face of the inspection target; (2) a step of supplying a particle-containing gas to the one end face of the inspection target under pressure, applying a second laser beam so that the second laser beam travels near the other end face of the inspection target parallel to the other end face of the inspection target, and photographing the other end face of the inspection target perpendicularly to the other end face of the inspection target; and (3) a step of specifying a defect in the inspection target from the photographic results obtained by the steps (1) and (2).

[2] The method according to [1], wherein the step (3) includes specifying a defect in the inspection target from a total image luminance of the photographic results obtained by the steps (1) and (2).

[3] The method according to [1] or [2], wherein the first laser beam is opposite to the second laser beam in a same plane.

[4] The method according to [3], further comprising: (4) a step of supplying a particle-containing gas to the one end face of the inspection target under pressure, (A) applying a third laser beam so that the third laser beam (a) travels near the other end face of the inspection target parallel to the other end face of the inspection target, and (b) perpendicularly intersects the first laser beam and the second laser beam in the same plane as the first laser beam and the second laser beam, and (B) photographing the other end face of the inspection target perpendicularly to the other end face of the inspection target; and (5) a step of supplying a particle-containing gas to the one end face of the inspection target under pressure, (C) applying a fourth laser beam so that the fourth laser beam (c) travels near the other end face of the inspection target parallel to the other end face of the inspection target, and (d) perpendicularly intersects the first laser beam and the second laser beam and is opposite to the third laser beam in the same plane as the first laser beam, the second laser beam, and the third laser beam, and (D) photographing the other end face of the inspection target perpendicularly to the other end face of the inspection target, (3)' the step of specifying a defect in the inspection target including specifying a defect in the inspection target from the photographic results obtained by the steps (1) and (2) and the photographic results obtained by the steps (4) and (5).

[5] The method according to [1] or [2], wherein the first laser beam and the second laser beam travel along different planes that are parallel to each other.

[6] A method of inspecting a defect in an inspection target, the method comprising: supplying a particle-containing gas to one end face of the inspection target under pressure, simultaneously applying a first laser beam and a second laser beam so that the first laser beam and the second laser beam travel near the other end face of the inspection target parallel to the other end face of the inspection target, and the first laser beam is opposite to the second laser beam in a same plane, and photographing the other end face of the inspection target perpendicularly to the other end face of the inspection target; and specifying a defect in the inspection target from the photographic result.

[7] A method of inspecting a defect in an inspection target, the method comprising: (1) a step of applying a laser beam so that the laser beam travels near the other end face of the inspection target parallel to the other end face of the inspection target, and photographing the other end face of the inspection target perpendicularly to the other end face of the inspection target; (2) a step of supplying a particle-containing gas to the one end face of the inspection target under pressure, applying a laser beam so that the laser beam travels near the other end face of the inspection target parallel to the other end face of the inspection target, and photographing the other end face of the inspection target perpendicularly to the other end face of the inspection target; and (3) a step of specifying a defect in the inspection target from the photographic results obtained by the steps (1) and (2).

[8] The method according to any one of [1] to [7], wherein at least one of the laser beam and the first to fourth laser beams is planarly emitted along a plane parallel to the other end face of the inspection target.

[9] An apparatus that inspects a defect in an inspection target, the apparatus comprising: particle supply means that supplies a particle-containing gas to one end face of the inspection target under pressure; first laser beam irradiation means and second laser beam irradiation means that apply a laser beam so that the laser beam travels near the other end face of the inspection target parallel to the other end face of the inspection target; photographing means that is disposed perpendicularly to the other end face of the inspection target and photographs the other end face of the inspection target; and defect specifying means that specifies a defect in the inspection target from a plurality of images photographed by the photographing means.

[10] The apparatus according to [9], wherein at least one of the first laser beam irradiation means and the second laser beam irradiation means includes means that diffuses the laser beam along a plane parallel to the other end face of the inspection target.

The effects of noise that occurs when the inspection target shines can be reduced by utilizing the method and the apparatus according to the present invention when inspecting a defect in the inspection target using particles and a laser beam.

EXPLANATION OF SYMBOLS

1: particle supply means, 3: (first) laser beam irradiation means, 4: third laser beam irradiation means, 5: second laser beam irradiation means, 6: fourth laser beam irradiation means, 7: photographing (light detection) means, 9: defect specifying means (computer), 11: inspection target (honeycomb structure), 13: normal light source, 15: particle source, 17: air source, 19: particle-containing air, 21: particle-containing air that has passed through inspection target, 23: laser beam, 25: partition wall, 27: through hole, 29: particle, 31: partition wall opposite to laser beam, 33, 35: bright spot, 37: defect

DETAILED DESCRIPTION OF THE INVENTION

Preferred embodiments of the present invention are described below. Note that the present invention is not limited to the following embodiments.

[Basic Principle]

The principle of the present invention is described in detail below taking an example of detecting a defect in a honeycomb structure shown in FIG. 1. Note that the present invention may be applied to various inspection targets that differ in shape and material in addition to a honeycomb structure.

Figure 1:
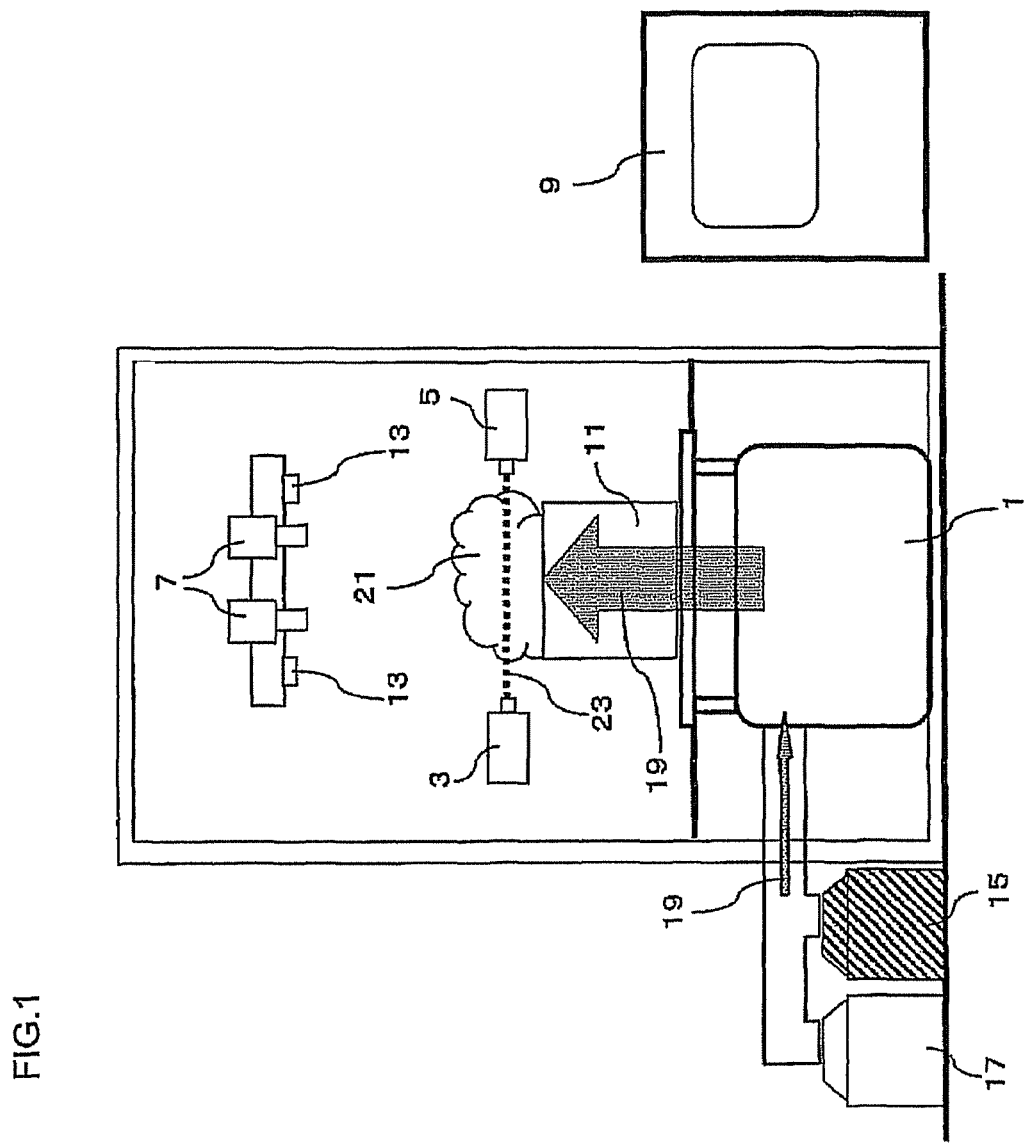
FIG. 1 is a schematic front view showing an apparatus according to a first embodiment of the present invention.

When an inspection target 11 shown in FIG. 1 is a honeycomb structure that is configured so that the ends of through holes are alternately plugged and particulate matter is collected and removed by a porous partition wall, particle-containing air 19 is introduced into the inspection target 11 (honeycomb structure) through one end face of the inspection target 11. The particle-containing air 19 introduced into the inspection target 11 passes through the porous partition wall of the inspection target 11, and is discharged through the other end face of the inspection target 11. When applying a laser beam in the direction parallel to the other end face of the inspection target 11 so that the laser beam is not applied to the inspection target 11 (honeycomb structure), particles contained in particle-containing air 21 that has passed through the inspection target causes the laser beam to undergo diffuse reflection so that the particles are visualized. When the inspection target 11 has a large defect, a number of large particles are discharged from the through hole having the defect, and cause the laser beam to undergo diffuse reflection to a large extent. Therefore, since the laser beam undergoes diffuse reflection to a large extent in an area having a large defect, the through hole having the defect can be detected. According to the present invention, a defect in the inspection target is specified based on scattered light that occurs when applying a first laser beam and scattered light that occurs when applying a second laser beam. This makes it possible to reduce noise that occurs when the inspection target shines due to secondary reflection of the laser beam.

First Embodiment

An inspection apparatus according to the present invention is described below with reference to FIG. 1. FIG. 1 shows an inspection apparatus according to a preferred embodiment of the present invention. In FIG. 1, the inspection apparatus according to the present invention includes a particle supply means 1, a first laser beam irradiation means 3, a second laser beam irradiation means 5, and a CCD camera (i.e., photographing means 7).

A particle source 15 includes a supersonic humidifier, and produces mist. The particle source used in the present invention is not particularly limited. The particle source may be a device that produces water particles using an atomizer, a supersonic humidifier, or the like, a device that burns incense (e.g., incense stick), a device that produces particles by spraying a glycol and/or water, a commercially available particle generator, a device that generates (supplies) powdery particles (e.g., calcium carbonate) using a vibration device or a blower, or the like.

Particles generated by the particle source 15 and air supplied from an air source 17 are mixed to form particle-containing air 19, and introduced into the particle supply means 1. A particle inlet (not shown) through which the particles are introduced from the particle supply means 1 into the inspection target 11 is provided in the upper area of the particle supply means 1. A pressurization mechanism (not shown) is also provided as a means that introduces the particle-containing air 19 into the inspection target 11. The inside of the particle supply means is pressurized by the pressurization mechanism, and the particle-containing air 19 contained in the particle supply means 1 is introduced into the inspection target 11 through the particle inlet. The pressurization mechanism is preferably a compressor that includes a regulator or the like from the viewpoint of maintaining a constant pressure inside the particle supply means 1. The inside of the particle supply means is preferably pressurized to 1 to 30 Pa when the inspection target is a porous article, or 100 to 20,000 Pa when the inspection target is a non-porous article. It is preferable that the pressurization mechanism pressurize the inside of the particle supply means within such a range.

The particle supply means 1 includes a manometer and a particle concentration meter so that the pressure and the particle concentration inside the particle supply means 1 can be managed. It is also possible to provide a particle circulation inlet and a particle circulation tube for returning the discharged particles to the particle supply means 1. The inspection apparatus according to the present invention shown in FIG. 1 is configured to inspect one inspection target 11. The particle inlet is provided with a lid (not shown) connected to a cylinder (not shown) so that the particle inlet can be opened and closed due to the upward and downward movement of the cylinder (not shown). This makes it possible to close the particle inlet that is not used.

An installation stage (not shown) that has an opening connected to the particle inlet is provided over the particle inlet so that the inspection target 11 can be removably installed on the installation stage. The inspection target 11 is installed on the installation stage in a state in which the outer circumferential surface of the inspection target 11 is sealed by a seal (not shown). The seal may have an appropriate shape corresponding to the shape of the inspection target 11. Since the installation stage has the above configuration, all of the particles that have passed through the particle inlet are introduced into the inspection target 11.

The first laser beam irradiation means 3 and the second laser beam irradiation means 5 are provided above the inspection target 11. It is preferable that the first laser beam irradiation means 3 and the second laser beam irradiation means 5 be able to move upward and downward. The first laser beam irradiation means 3 and the second laser beam irradiation means 5 are preferably provided so that the laser beams travel within the range of 5 mm or less, and more preferably 3 mm or less from the discharge side of the inspection target 11 during inspection. It is preferable to dispose the first laser beam irradiation means 3 and the second laser beam irradiation means 5 so that the first laser beam is opposite to the second laser beam in a same plane. When the inspection target 11 is a honeycomb structure that has through holes (cells) having a square cross-sectional shape, it is preferable to dispose the laser beam irradiation means 3 and 5 in the diagonal direction of the cells of the honeycomb structure. A lens as a means that diffuses the laser beam in one plane is provided in front of each of the first laser beam irradiation means 3 and the second laser beam irradiation means 5 so that the laser beam travels in one plane parallel to the end face of the inspection target 11 that discharges the particle-containing air 21 that has passed through the inspection target 11.

In FIG. 1, an He—Ne laser beam generator is provided as a light generator. Note that the light generator means used in the present invention is not particularly limited insofar as the light generator means generates light that has high directivity and has a wavelength that allows diffuse reflection to occur due to the particles generated by the particle generating means. It is preferable that the light generator means generate a laser beam. For example, the light generator means may be a solid-state laser, a gas laser, a semiconductor laser, a dye laser, an excimer laser, a free electron laser, or the like. Examples of the light generated by the light generator means include a red laser beam (wavelength: about 650 nm), a green laser beam (wavelength: about 532 nm), a purple laser beam (wavelength: about 400 nm), and the like.

The CCD camera (i.e., photographing means 7) is provided above the inspection target 11 to face vertically downward so that the laser beam that has undergone diffuse reflection can be photographed and recorded. As the photographing means 7, a camera, an optical video camera, or the like may be used instead of the CCD camera. An air purge mechanism that applies a pressure to prevent the particles from adhering to the lens of the CCD camera may be disposed vertically under the CCD camera.

A normal light source 13 is disposed near the photographing means 7. The photographing means 7 may not be able to visually observe the inspection target 11 depending on the particle concentration in the particle-containing air 21 that has passed through the inspection target. Therefore, the inspection target 11 may be photographed by the photographing means 7 using the normal light source 13 before supplying the particle-containing air to the inspection target 11, and the position of a defect in the inspection target 11 may be specified using the image photographed before supplying the particle-containing air and an image photographed while supplying the particle-containing air.

In FIG. 1, a computer is provided as a defect specifying means 9. The defect specifying means 9 specifies a defect in the inspection target 11 from the photographic results obtained by the photographing means 7 (i.e., scattered light of the first laser beam and scattered light of the second laser beam). A normal computer may be used as the defect specifying means 9.

The entire configuration of a detection method according to the present invention is described below. First, particles are generated. The particles may be generated by an arbitrary method. For example, a method that burns incense (e.g., incense stick), a method that produces particles by spraying a glycol and/or water, a method that produces water particles using solid carbon dioxide, liquid nitrogen, an atomizer, a supersonic humidifier, or the like, a method using a commercially available particle generator, a method that generates powdery particles (e.g., calcium carbonate) using a vibration device or a blower, or the like may be used. The particle size of the particles generated by the particle generating means may be appropriately selected depending on the shape of the inspection target, the pore size of the inspection target (when the inspection target is a porous article), and the like. For example, a particle size appropriate for the inspection target may be selected by determining the relationship between the type of defect and the particle size distribution of particles discharged. When the inspection target is a porous article, the amount of particles trapped inside the pores formed in the porous article increases to a large extent if the particle size is too large. This makes it necessary to remove the particles by a post-treatment. If the particle size is too small, the amount of particles discharged changes to only a small extent due to the presence or absence of a defect. The particle size is preferably 0.3 to 200 μm, more preferably 0.5 to 50 μm, and still more preferably 1 to 10 μm. Note that particles having a particle size outside the above range may be included in the particles generated by the particle generating means to such an extent that the object of the present invention can be achieved. It is preferable that the particles generated by the particle generating means do not change in particle size with the passage of time.

The generated particles are introduced in the inspection target. The particles may be introduced into the inspection target by an arbitrary method. For example, it is preferable to accumulate the particles in a particle chamber until a given concentration is reached, and apply a given pressure to introduce the particles into the inspection target, or provide a conduit above the inspection target, and discharge air using a fan or the like to introduce the particles into the inspection target from the particle chamber. The concentration of the particles introduced into the inspection target is not particularly limited. The concentration of the particles introduced into the inspection target may be appropriately selected so that the particles can be detected by applying light with high directivity (e.g., laser beam) and a defect area can be clearly distinguished from other areas. The pressure applied is not particularly limited, and may be appropriately selected depending on the type and the shape of the inspection target and the like. The pressure loss in the inspection target decreases as the number of defects increases or the size of a defect increases. In this case, the defect can be detected by applying a low pressure. On the other hand, the pressure loss in the inspection target increases as the number of defects decreases or the size of a defect decreases. In this case, it is necessary to apply a high pressure. The particles discharged from the inspection target flow over a long distance in a laminar flow by applying a high pressure so that the defect can be detected even if light travels apart from the inspection target. However, when the inspection target is a porous article, a large number of particles flow through the porous article if too high a pressure is applied. Therefore, it may be necessary to increase the amount of particles supplied, or it may be difficult to recover the particles. This results in an increase in cost.

The shape, the material, the pore size (i.e., porous article), the application, and the like of the inspection target are not particularly limited insofar as a defect may be detected in the inspection target. The method according to the present invention may be applied to various inspection targets that differ in shape, material, pore size (i.e., porous article), application, and the like. For example, when the inspection target is a porous article, the inspection target is preferably configured so that the treatment target fluid is discharged from a planar area. In the present invention, the inspection target is preferably configured so that the particles are discharged from a planar area irrespective of whether or not the inspection target is a porous article. The present invention may be preferably applied to the case where the inspection target is a porous article. The inspection target may preferably be an article (e.g., honeycomb structure) for which a defect cannot be easily detected from the outside. The inspection target may be more preferably an article used for a diesel particulate filter, a high-temperature gas collection apparatus, and the like. It is also preferable that the inspection target be a non-porous article that forms a porous article upon firing (e.g., unfired honeycomb structure), since a defect can be detected before firing. In this case, it is preferable that the inspection target be a non-porous article that has been formed into a given shape and dried to keep its shape.

Light with high directivity is then applied so that the light travels near the inspection target, and a state in which the light undergoes diffuse reflection due to the particles discharged from the inspection target is photographed to detect a defect. A camera, an optical video camera, a CCD camera, or the like is suitably used to record the photographed image.

The defect specifying means 9 processes the image photographed by the photographing means 7 to specify the defect in the inspection target 11. The defect may be specified by an arbitrary method. For example, the following method may be used.

Figure 2:
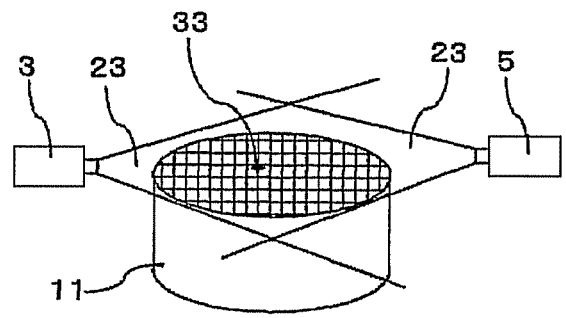
FIG. 2 is a schematic perspective view showing the principle of the first embodiment of the present invention.

In this embodiment, the first laser beam irradiation means 3 and the second laser beam irradiation means 5 are disposed to face each other (see FIG. 1). FIG. 2 is a perspective view showing a state in which the first laser beam irradiation means 3 and the second laser beam irradiation means 5 face each other. A laser beam 23 is scattered upon collision with the particles. The laser beam scattered in the direction of the photographing means 7 is detected by the photographing means 7 as a bright spot. This makes it possible to detect the presence of the particles (i.e., defect). In this case, the laser beam scattered by the particles may cause the edge of the inspection target 11 opposite to the laser beam irradiation means to shine (secondary reflected light) and to be detected by the photographing means 7 as a bright spot. It is difficult to distinguish the bright spot due to the particles from the bright spot on the inspection target 11 due to secondary reflected light. According to this embodiment, however, since the first laser beam irradiation means 3 and the second laser beam irradiation means 5 are disposed to face each other, the bright spot that occurs at the edge of the end face of the inspection target 11 due to the laser beam applied from the first laser beam irradiation means 3 does not occur due to the laser beam applied from the second laser beam irradiation means 5, and the bright spot that occurs at the edge of the end face of the inspection target 11 due to the laser beam applied from the second laser beam irradiation means 5 does not occur due to the laser beam applied from the first laser beam irradiation means 3. On the other hand, the bright spot due to the particles occurs when the laser beam is applied from the first laser beam irradiation means 3 and when the laser beam is applied from the second laser beam irradiation means 5. Therefore, when calculating the total luminance from the image of scattered light due to the first laser beam and the image of scattered light due to the second laser beam, since the bright spot that occurs at the edge of the end face of the inspection target 11 is observed on only one of the images, the total luminance is the same as the luminance before calculating the total luminance. On the other hand, the total luminance of the bright spot due to the particles is almost twice the luminance of the bright spot due to the particles before calculating the total luminance. Therefore, the SN ratio increases.

The defect specifying means 9 synthesizes the image of scattered light due to the first laser beam and the image of scattered light due to the second laser beam that are photographed by the photographing means 7 so that the plane coordinates of the images coincide with each other. The defect specifying means 9 then quantifies the luminance of the synthesized image. The defect specifying means 9 then specifies the coordinates at which the luminance is equal to or higher than a given value (threshold value). The coordinates thus specified indicate the defect in the inspection target 11. The threshold value may be appropriately selected between the luminance of the bright spot at the edge of the end face of the inspection target 11 and the luminance of the bright spot due to the particles after synthesis.

Although this embodiment has been described taking an example of providing the first laser beam irradiation means and the second laser beam irradiation means, three or more laser beam irradiation means may be provided. Specifically, (A) a third laser beam irradiation means may be disposed to apply a third laser beam so that the third laser beam (a) travels near the other end face of the inspection target parallel to the other end face of the inspection target, and (b) perpendicularly intersects the first laser beam and the second laser beam in the same plane as the first laser beam and the second laser beam, and (C) a fourth laser beam irradiation means may be disposed to apply a fourth laser beam so that the fourth laser beam (c) travels near the other end face of the inspection target parallel to the other end face of the inspection target, and (d) perpendicularly intersects the first laser beam and the second laser beam and is opposite to the third laser beam in the same plane as the first laser beam, the second laser beam, and the third laser beam. In this case, a defect in the inspection target is specified from the photographic results for scattered light due to the first to fourth laser beam irradiation means.

Figure 3:
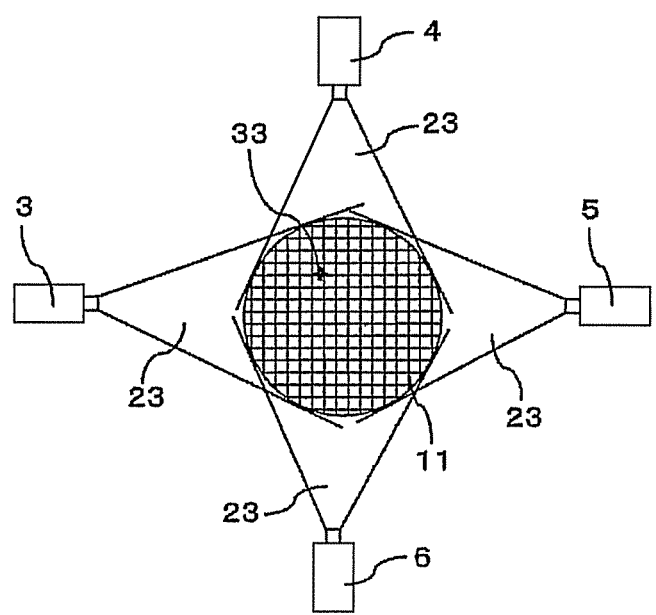
FIG. 3 is a schematic plan view showing a modification of the first embodiment of the present invention.

FIG. 3 is a schematic plan view showing the above state. The first laser beam irradiation means 3, the second laser beam irradiation means 5, a third laser beam irradiation means 4, and a fourth laser beam irradiation means 6 are disposed in a same plane. The laser beams 23 emitted from the first to fourth laser beam irradiation means travel in a same plane near the end face of the inspection target 11 parallel to the end face of the inspection target 11. This configuration makes it possible to effectively enhance only the luminance of the bright spot due to the particles so that the detection sensitivity increases.

Although this embodiment has been described taking an example in which the first to second (fourth) laser beams are separately emitted, the first to second (fourth) laser beams may be emitted simultaneously. This configuration makes it possible to enhance only the luminance of the bright spots due to the particles by a single photographing operation. Therefore, detection is affected by a temporal change (e.g., when smoke moves to a large extent) to only a small extent as compared with the case where the total luminance is calculated from a plurality of photographing operations. Moreover, since the defect specifying means 9 need not synthesize the photographed images, the process of the defect specifying means 9 can be simplified.

In this embodiment, the first to second (fourth) laser beams may be emitted and photographed a plurality of times. In this case, the first laser beam may be emitted and photographed a plurality of times, and the second laser beam may then be emitted and photographed. Alternatively, the first to second (fourth) laser beams may be emitted and photographed in cycles. The luminance of an area other than the bright spot due to the particles is made more uniform (averaged) by synthesizing the resulting images, so that the SN ratio when determining a defect further increases.

Second Embodiment

Figure 4:
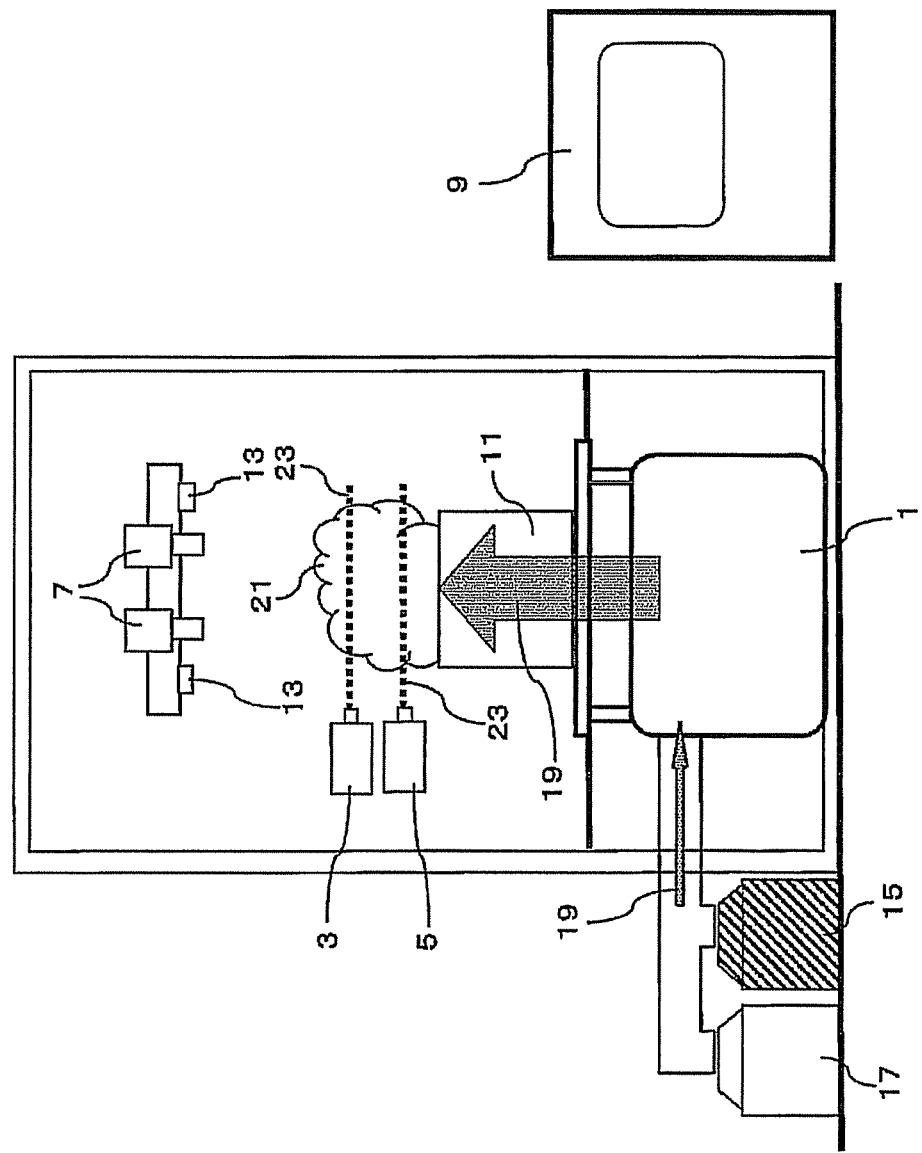
FIG. 4 is a schematic front view showing an apparatus according to a second embodiment of the present invention.

FIG. 4 is a schematic front view showing a second embodiment of the present invention. The second embodiment shown in FIG. 4 differs from the first embodiment in that the first laser beam irradiation means 3 and the second laser beam irradiation means 5 are disposed so that the first laser beam and the second laser beam travel along different planes that are parallel to each other. The difference from the first embodiment is described below.

Figure 5:
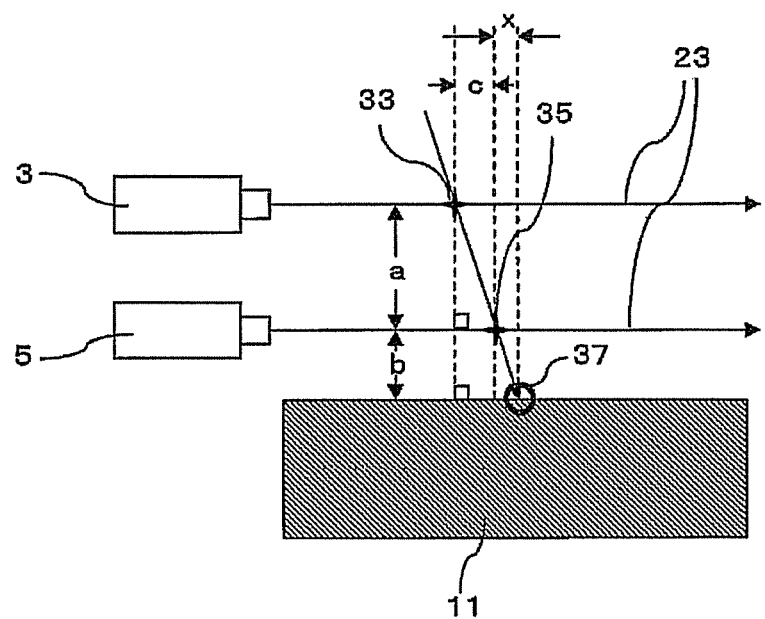
FIG. 5 is a schematic front view showing the principle of the second embodiment of the present invention.

FIG. 5 is a schematic front view showing the principle of the second embodiment of the present invention. The particles that have passed through a defect 37 in the inspection target 11 may move away from the position directly above the defect 37 due to an air stream around the inspection target 11 (see bright spots 33 and 35). Therefore, it is preferable to cause the laser beam to travel near the end face of the inspection target 11. However, the laser beam scattered by the particles may be reflected by the edge of the end face of the inspection target 11 (i.e., the edge of the end face of the inspection target 11 shines), and may serve as noise.

If the laser beam travels at a sufficient distance from the end face of the inspection target 11, a situation in which the laser beam scattered by the particles is reflected by the edge of the end face of the inspection target 11 (i.e., the edge of the end face of the inspection target 11 shines) can be suppressed. In this case, if the distance between the end face of the inspection target 11 and the laser beam is about 5 to 50 mm, a situation in which the laser beam scattered by the particles is reflected by the edge of the end face of the inspection target 11 can be sufficiently suppressed. In this embodiment, the first laser beam irradiation means 3 and the second laser beam irradiation means 5 are disposed so that the first laser beam and the second laser beam travel along different planes that are parallel to each other in order to deal with a problem in which the particles that have passed through the defect 37 in the inspection target 11 move away from the position directly above the defect 37 due to an air stream around the inspection target 11 so that the defect 37 in the inspection target 11 cannot be specified.

As shown in FIG. 5, the vertical distance b between the inspection target 11 and the laser beam 23 emitted from the second laser beam irradiation means 5, and the vertical distance a between the laser beam 23 emitted from the second laser beam irradiation means 5 and the laser beam 23 emitted from the first laser beam irradiation means 3 are measured in advance. The position x of the defect 37 can be specified by measuring the distance c between the bright spot 33 and the bright spot 35 photographed by the photographing means 7 (see FIG. 4) that is perpendicular to the end face of the inspection target 11. Specifically, since the relationship "a:b=c:x" is satisfied in FIG. 5, the position x of the defect 37 is indicated by "x=bc/a".

The bright spot 33 due to the laser beam 23 emitted from the first laser beam irradiation means 3 can be distinguished from the bright spot 35 due to the laser beam 23 emitted from the second laser beam irradiation means 5 by causing the first laser beam irradiation means 3 and the second laser beam irradiation means 5 to emit the laser beams at different timings. Alternatively, the bright spot 33 due to the laser beam 23 emitted from the first laser beam irradiation means 3 may be distinguished from the bright spot 35 due to the laser beam 23 emitted from the second laser beam irradiation means 5 by utilizing lasers that differ in frequency (color) as the first laser beam irradiation means 3 and the second laser beam irradiation means 5.

The process of specifying the defect in the inspection target 11 from the bright spot 33 due to the laser beam 23 emitted from the first laser beam irradiation means 3 and the bright spot 35 due to the laser beam 23 emitted from the second laser beam irradiation means 5 that are photographed by the photographing means 7 may be implemented by the defect specifying means 9 using a known method.

In this embodiment, the first and second laser beams may be emitted and photographed a plurality of times. In this case, the first laser beam may be emitted and photographed a plurality of times, and the second laser beam may then be emitted and photographed. Alternatively, the first and second laser beams may be emitted and photographed in cycles. The luminance of the area other than the bright spots due to the particles is made more uniform (averaged) by synthesizing the resulting images, so that the SN ratio when determining a defect further increases.

Third Embodiment

Figure 6:
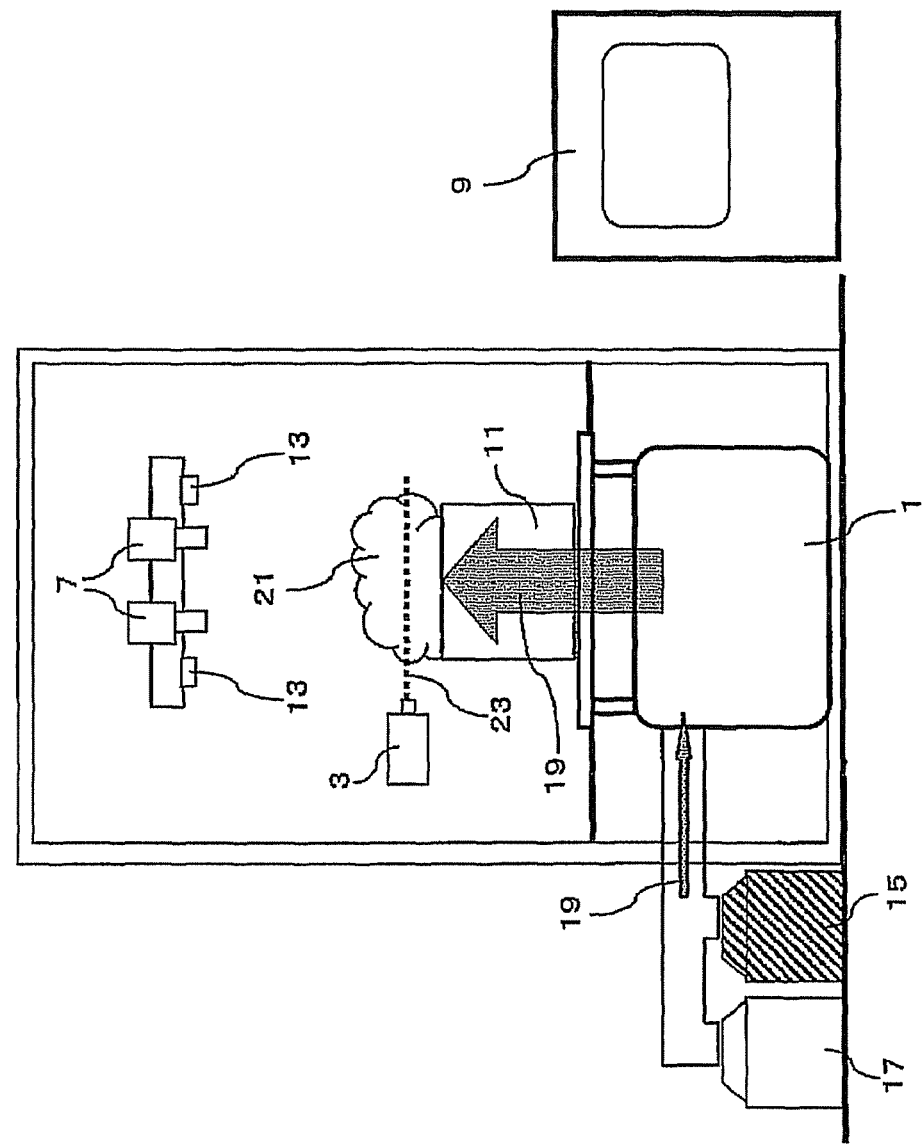
FIG. 6 is a schematic front view showing an apparatus according to a third embodiment of the present invention and related art.
Figure 7:
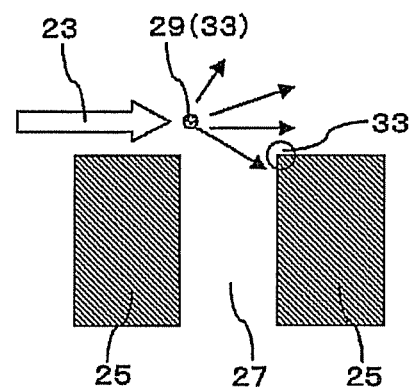
FIG. 7 is a schematic enlarged side view showing related art.
Figure 8:
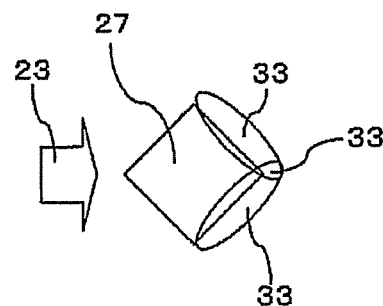
FIG. 8 is a plan view of FIG. 7.

FIG. 6 is a schematic front view showing a third embodiment of the present invention. The third embodiment shown in FIG. 6 differs from the first embodiment in that only a single laser beam irradiation means is provided. The difference from the first embodiment is described below.

In this embodiment, a laser beam is applied so that the laser beam travels near the end face of the inspection target parallel to the end face of the inspection target without supplying a particle-containing gas, and the end face of the inspection target is photographed perpendicularly to the end face of the inspection target. A particle-containing gas is then supplied to one end face of the inspection target under pressure, a laser beam is applied so that the laser beam travels near the other end face of the inspection target parallel to the other end face of the inspection target, and the other end face of the inspection target is photographed perpendicularly to the other end face of the inspection target. A defect in the inspection target is specified from the resulting photographic results.

A laser beam has high directivity. However, a laser beam may be diffused depending on a lens used to obtain a planar laser beam, or during a scan used to obtain a planar laser beam. In this case, the edge of the end face of the inspection target may shine due to the diffused laser beam. This embodiment reduces the effects of such a phenomenon.

Specifically, when a laser beam is applied so that it travels near the end face of the inspection target parallel to the end face of the inspection target without supplying a particle-containing gas, and the end face of the inspection target is photographed perpendicularly to the end face of the inspection target, the end face of the inspection target can be photographed without being affected by scattering due to the particles. If the edge of the end face of the inspection target shines, this is due to the diffused laser beam.

A particle-containing gas is then supplied to one end face of the inspection target under pressure, a laser beam is applied to travel near the other end face of the inspection target parallel to the other end face of the inspection target, and the other end face of the inspection target is photographed perpendicularly to the other end face of the inspection target.

A defect in the inspection target 11 can be specified by calculating the difference in luminance data between the two photographed images. The image data may be processed by the defect specifying means 9 using a known method.

INDUSTRIAL APPLICABILITY

The present invention may be used to detect a defect when producing a honeycomb structure, for example.

The invention claimed is:

1. A method of inspecting a defect in an inspection target, the method comprising:
   (1) a step of supplying a particle-containing gas to one end face of the inspection target under pressure, using a laser to apply a first laser beam so that the first laser beam travels near the other end face of the inspection target in a first direction parallel to the other end face of the inspection target, and photographing the other end face of the inspection target perpendicularly to the other end face of the inspection target;
   (2) a step of supplying a particle-containing gas to the one end face of the same inspection target under pressure, using a laser to apply a second laser beam so that the second laser beam travels near the other end face of the same inspection target in a second direction parallel to the other end face of the same inspection target, and photographing the other end face of the sets inspection target perpendicularly to the other end face of the same inspection target; and
   (3) a step of specifying a defect in the same inspection target from the photographic results obtained by the steps (1) and (2).

2. The method according to claim 1, wherein the step (3) includes specifying a defect in the same inspection target from a total image luminance of the photographic results obtained by the steps (1) and (2).

3. The method according to claim 1, wherein the first laser beam is opposite to the second laser beam in a same plane.

4. The method according to claim 3, further comprising:
- (4) a step of supplying a particle-containing gas to the one end face of the same inspection target under pressure, (A) using a laser to apply a third laser beam so that the third laser beam (a) travels near the other end face of the same inspection target parallel to the other end face of the same inspection target, and (b) perpendicularly intersects the first laser beam and the second laser beam in the same plane as the first laser beam and the second laser beam, and (B) photographing the other end face of the same inspection target perpendicularly to the other end face of the same inspection target; and
- (5) a step of supplying a particle-containing gas to the one end face of the same inspection target under pressure, (C) using a laser to apply a fourth laser beam so that the fourth laser beam (c) travels near the other end face of the same inspection target parallel to the other end face of the same inspection target, and (d) perpendicularly intersects the first laser beam and the second laser beam and is opposite to the third laser beam in the same plane as the first laser beam, the second laser beam, and the third laser beam, and (D) photographing the other end face of the same inspection target perpendicularly to the other end face of the same inspection target,
- (3)' the step of specifying a defect in the same inspection target including specifying a defect in the same inspection target from the photographic results obtained by the steps (1) and (2) and the photographic results obtained by the steps (4) and (5).

5. The method according to claim 1, wherein the first laser beam and the second laser beam travel along different planes that are parallel to each other.

6. A method of inspecting a defect in an inspection target, the method comprising:
- supplying a particle-containing gas to one end face of the inspection target under pressure, using first and second lasers to simultaneously apply a first laser beam and a second laser beam so that the first laser beam and the second laser beam travel near the other end face of the same inspection target parallel to the other end face of the same inspection target, and the first laser beam is opposite to the second laser beam in a same plane, and photographing the other end face of the same inspection target perpendicularly to the other end face of the same inspection target; and
- specifying a defect in the same target from the photographic result.

7. A method of inspecting a defect in an inspection target, the method comprising:
- (1) a step of using a laser to apply a laser beam so that the laser beam travels near the other end face of the inspection target parallel to the other end face of the inspection target, and photographing the other end face of the inspection target perpendicularly to the other end face of the inspection target;
- (2) a step of supplying a particle-containing gas to the one end face of the ace inspection target under pressure, using a laser to apply a laser beam so that the laser beam travels near the other end face of the same inspection target parallel to the other end face of the same inspection target, and photographing the other end face of the same inspection target perpendicularly to the other end face of the same inspection target; and
- (3) a step of specifying a defect in the same inspection target from the photographic results obtained by the steps (1) and (2).

8. The method according to claim 1, wherein at least one of the laser beam and the first to fourth laser beams is planarly emitted along a plane parallel to the other end face of the same inspection target.

9. The method according to claim 6, wherein at least one of the laser beam and the first to fourth laser beams is planarly emitted along a plane parallel to the other end face of the same inspection target.

10. The method according to claim 7, wherein at least one of the laser beam and the first to fourth laser beams is planarly emitted along a plane parallel to the other end face of the same inspection target.

11. An apparatus that inspects a defect in an inspection target, the apparatus comprising:
- particle supply means that supplies a particle-containing gas to one end face of the inspection target under pressure;
- first laser beam irradiation means and second laser beam irradiation means that apply respective laser beams that travel near the other end face of the same inspection target in different directions parallel to the other end face of the same inspection target;
- photographing means that is disposed perpendicularly to the other end face of the same inspection target and photographs the other end face of the same inspection target; and
- defect specifying means that specifies a defect in the same inspection target from a plurality of images photographed by the photographing means.

12. The apparatus according to claim 11, wherein at least one of the first laser beam irradiation means and the second laser beam irradiation means includes means that diffuses the laser beam along a plane parallel to the other end face of the same inspection target.

* * * * *

UNITED STATES PATENT AND TRADEMARK OFFICE
CERTIFICATE OF CORRECTION

PATENT NO. : 8,422,014 B2  Page 1 of 1
APPLICATION NO. : 12/712419
DATED : April 16, 2013
INVENTOR(S) : Tatsuhiko Hatano, Kouichi Miyashita and Isao Shikata It is certified that error appears in the above-identified patent and that said Letters Patent is hereby corrected as shown below:

In the Claims

Column 12, line 62

(claim 1, line 17): Change "sets" to -- same --

Column 14, line 10

(claim 7, line 10): Change "ace" to -- same --

Signed and Sealed this
Twenty-fifth Day of June, 2013

Teresa Stanek Rea
*Acting Director of the United States Patent and Trademark Office*